United States Patent [19]
Baugh et al.

[11] Patent Number: 5,925,319
[45] Date of Patent: Jul. 20, 1999

[54] TEST CARTRIDGE FOR EVALUATING BLOOD PLATELET FUNCTIONALITY

[75] Inventors: Robert F. Baugh, Parker; Carole G. Lane, Greenwood Village; Adrian C. Wilson, Denver, all of Colo.

[73] Assignee: Medtronic, Inc., Minneapolis, Minn.

[21] Appl. No.: 08/640,275

[22] Filed: Apr. 30, 1996

[51] Int. Cl.[6] ............... G01N 31/02; G01N 33/48
[52] U.S. Cl. .............. 422/73; 422/68.1; 435/288.4; 435/304.2
[58] Field of Search ............... 422/73, 63, 68.1, 422/102, 61; 435/288.2, 288.4, 304.2, 305.2

[56] References Cited

U.S. PATENT DOCUMENTS

| | | | |
|---|---|---|---|
| 3,077,106 | 2/1963 | Fink | 73/53 |
| 3,307,392 | 3/1967 | Owen et al. | 73/64.1 |
| 3,450,501 | 6/1969 | Oberhardt | 23/253 |
| 3,492,096 | 1/1970 | Hattersley | 23/230 |
| 3,560,162 | 2/1971 | Mittleman | 23/253 |
| 3,560,163 | 2/1971 | Mittleman | 23/253 |
| 3,587,295 | 6/1971 | Simons | 73/64.1 |
| 3,635,678 | 1/1972 | Seitz et al. | 23/230 R |
| 3,650,698 | 3/1972 | Adler | 23/253 R |
| 3,658,480 | 4/1972 | Kane et al. | 23/230 B |
| 3,692,487 | 9/1972 | Sanz | 23/253 R |
| 3,695,842 | 10/1972 | Mintz | 23/230 R |
| 3,699,437 | 10/1972 | Ur | 324/65 R |
| 3,704,099 | 11/1972 | Sanz | 23/253 R |
| 3,719,075 | 3/1973 | Mandrona et al. | 73/54 |
| 3,741,002 | 6/1973 | Simons | 73/64.1 |
| 3,814,585 | 6/1974 | Bailly | 23/230 B |
| 3,836,333 | 9/1974 | Mintz | 23/259 |
| 3,911,728 | 10/1975 | Fixot | 73/55 |
| 3,918,908 | 11/1975 | Moyer et al. | 23/230 B |
| 4,131,549 | 12/1978 | Ferrara | 210/518 |
| 4,197,735 | 4/1980 | Munzer et al. | 73/61.4 |
| 4,210,623 | 7/1980 | Breno et al. | 422/101 |
| 4,443,408 | 4/1984 | Mintz | 422/73 |
| 4,599,219 | 7/1986 | Cooper et al. | 422/61 |
| 4,752,449 | 6/1988 | Jackson et al. | 422/73 |
| 4,780,418 | 10/1988 | Kratzer | 436/69 |
| 4,782,026 | 11/1988 | Baugh et al. | 436/69 |
| 4,788,139 | 11/1988 | Ryan | 435/13 |
| 4,795,703 | 1/1989 | Folkman et al. | 435/13 |
| 4,871,677 | 10/1989 | Baugh et al. | 436/69 |
| 4,876,069 | 10/1989 | Jochimsen | 422/73 |
| 5,091,304 | 2/1992 | La Duca et al. | 435/13 |
| 5,174,961 | 12/1992 | Smith | 422/73 |
| 5,314,826 | 5/1994 | Baugh | 436/69 |

OTHER PUBLICATIONS

"Platelet activating factor. Evidence for 1–0–alkyl–2–acetyl–sn–glyceryl–3–phosphorylcholine as the active component (A new class of lipid chemical mediators)," C. A. Demopoulos, et al., *Journal of Biological Chemistry*, 254:9355–9358 (1979).

*Primary Examiner*—Lyle A. Alexander
*Attorney, Agent, or Firm*—Chrisman Bynum & Johnson; Steven C. Petersen

[57] ABSTRACT

Apparatus and method for evaluating platelet functionality of a blood sample. A cartridge includes a plurality of test cells. Each cell receives an aliquot part of a blood sample. A measured amount of clotting reagent is provided in each cell. A measured amount of platelet activation reagent is provided in each cell, the amount of such reagent in each cell differing from the amount of such reagent in each other cell. The relative clotting times of the aliquot samples in the cells are determinative of the platelet functionality of the blood sample.

25 Claims, 3 Drawing Sheets

TEST CARTRIDGE FOR EVALUATING BLOOD PLATELET FUNCTIONALITY

BACKGROUND OF THE INVENTION

1. Field of the Invention

The present invention relates to an apparatus for evaluating blood platelet functionality. More specifically, the invention relates to an improved multicell cartridge for use in evaluating blood platelet functionality and method for using the same.

2. Description of the Prior Art

It has been observed that blood platelets play a significant role in the clotting or coagulation of whole blood. When platelets are activated, they shorten the clotting time of the blood. This shortening is related to the initial status of the platelets and platelet disfunction is considered a leading cause of post-surgical bleeding following cardiopulmonary bypass surgery.

Blood platelet functionality is conventionally determined by mixing blood and a clot promoting reagent such as kaolin in a buffer solution. This is done in a series of test cells incorporated in a test cartridge. After adding the clotting reagent, the blood/kaolin solution in each cell is agitated to activate the platelets to promote clotting. The degree of agitation of the blood sample in each cell differs one from the other. As described in U.S. Pat. No. 5,314,826, the clotting time is proportional to the degree of agitation. By comparing clotting times of aliquots of the blood as a function of degree of agitation, the blood platelet functionality can be determined. This process and the apparatus for carrying it out are disclosed in detail in U.S. Pats. Nos. 4,599,219 and 5,314,826. Where necessary for a further understanding of the present invention, the disclosures in these two patents are incorporated by reference herein.

Chemical platelet activators or reagents are well-known in the art. One such activator, 1-O-alkyl-2acetyl-sn-glyceryl-3-phosphorylcholine, a biologically active phospholipid, is disclosed in Demopoulos, et al., J. Biol. Chem., 1979; 254:9355–8. This platelet activator or reagent, often referred to as a platelet activating factor, enhances the ability of active platelets to effectively participate in the blood clotting reaction and thereby shorten the clotting time of the blood. If the platelets are inactive or not functioning normally, the activator will have a lessened or no effect on the clotting time.

OBJECTS OF THE INVENTION

It is the principal object of the present invention to provide an improved platelet functionality test cartridge that facilitates the evaluation of functional platelets in a blood sample.

Another object of the present invention is to provide a test cartridge that, upon receipt of blood sample aliquots therein, provides clotting results that are predictive of platelet activity.

SUMMARY OF THE INVENTION

In accordance with the foregoing objects, the present invention is embodied in a cartridge having a plurality of test cells. Each cell is adapted for receiving an aliquot part of a blood sample. A measured amount of platelet activating reagent is applied in the reaction chamber of each cell as a dried fill. The amount of reagent in each cell differs from the amount of reagent in each other cell, at least one of the cells containing no platelet activating reagent. Additionally, amounts of heparin or protamine may be added in each cell either as a liquid or dried fill. The cells also include a clotting reagent such as kaolin which on use of the cartridge is inserted into the reaction chamber and mixed with the blood and platelet activating reagent. The relative clotting times of the samples in each of the cells is measured and, when compared to a standard and each other, determines the platelet functionality of the blood sample.

The cartridge and method of determining platelet functionality is useful in connection with open heart and cardiopulmonary surgery wherein the blood condition of the patient must be closely monitored.

DESCRIPTION OF THE PREFERRED EMBODIMENT

Figure 1:
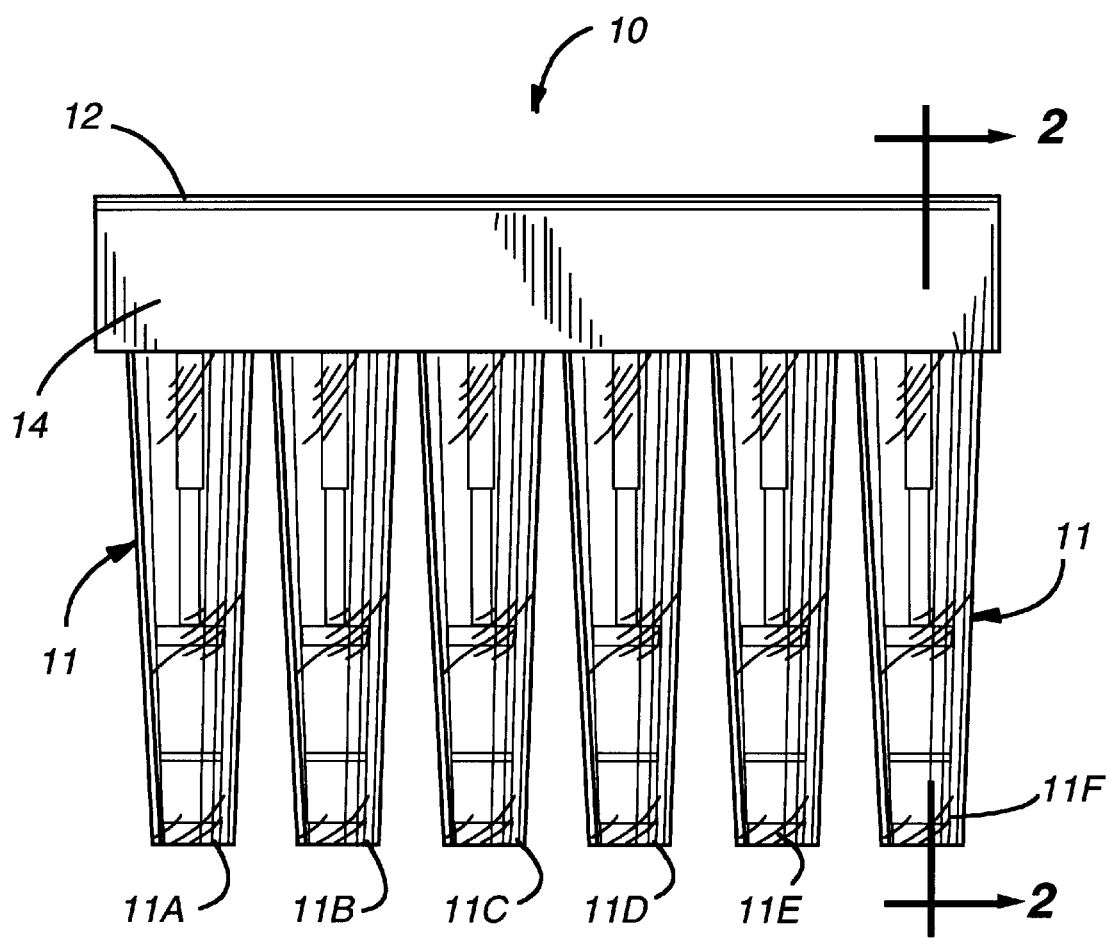
FIG. 1 is a front elevation view of a multicell cartridge embodying the present invention.
Figure 2:
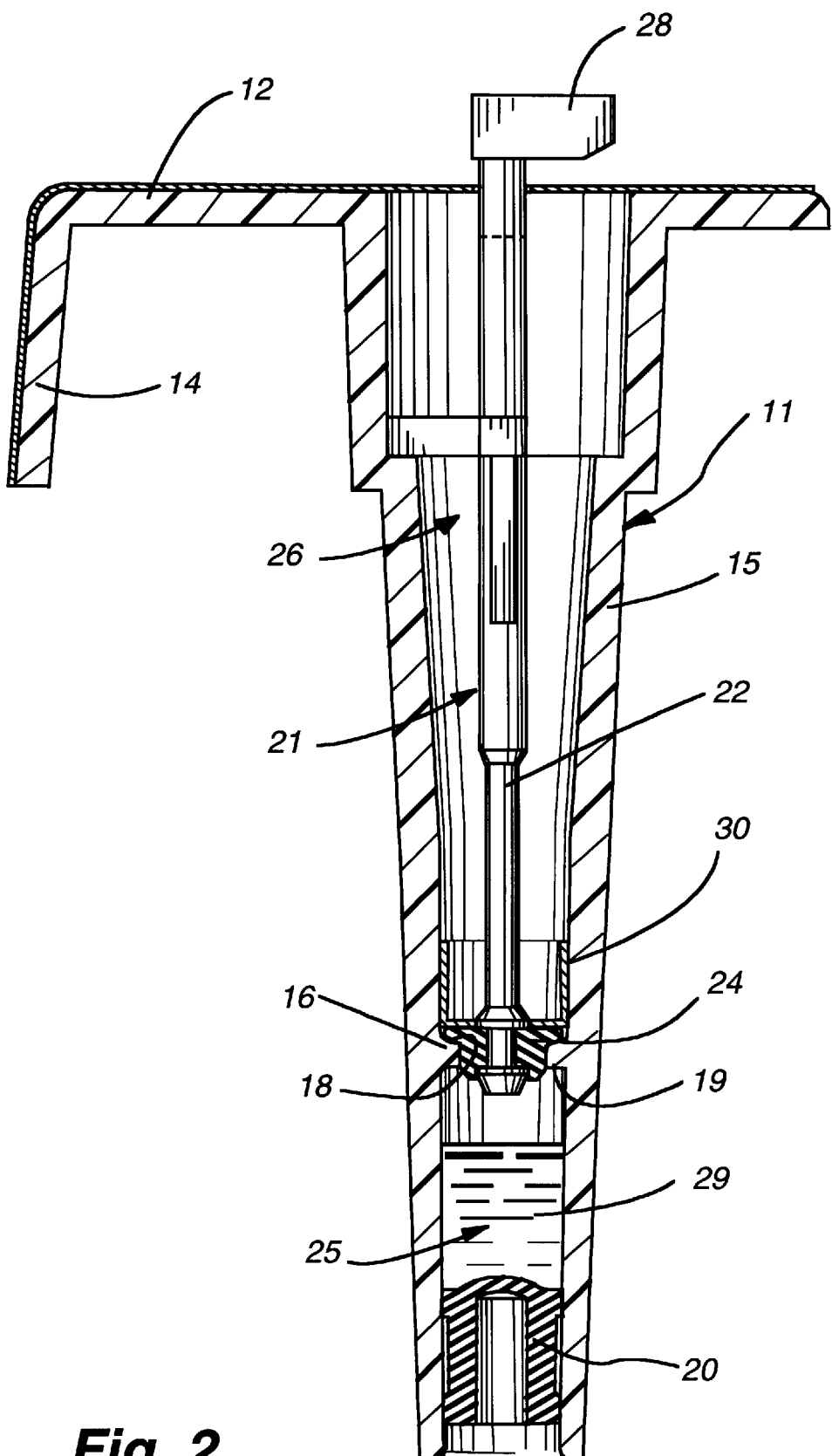
FIG. 2 is a section view taken substantially in the plane of line 2—2 on FIG. 1.

The present invention is embodied in a test cartridge 10 having a plurality of test cells 11, preferably six such cells, depending from and integral with a cartridge plate 12 having a front depending skirt or panel 14. The cartridge is adapted to be inserted into a test apparatus such as shown and described in detail in U.S. Pat. No. 4,599,219 for the determination of clotting time of an aliquot blood sample inserted into each test cell 11 as described in detail in said patent. Each cell is formed by a downwardly tapered tube 15 defining an inwardly projecting annular seat 16 intermediate its ends and in turn defining an upper sealing surface 18 and a lower sealing surface 19. A resilient flexible sliding plug 20 is positioned in the lower end of the tube 15 while a plunger 21 defined by a plunger shaft 22 and a sealing washer or disk 24 is positioned in the upper portion of the tube. The sealing washer 24 seats against the upper sealing surface 18 of the annular seat and defines with the plug 20 a lower clotting reagent chamber 25. The tube 15 defines above the washer 24 an upper cell reaction chamber 26. At its upper end the plunger 21 defines a flag 28 and is adapted for engagement by the test machine (not shown).

A clotting reagent 29, such as kaolin in a buffered, bacteriostatic solution, is contained in the clotting reagent chamber 25 above the plug 20 and below the seal washer 24. When the cartridge is used, the plunger 21 of each cell is lifted and the plug 20 is pushed upwardly, thereby forcing the clotting reagent into the blood sample contained in the upper cell reaction chamber 26 to initiate clotting.

In accordance with the present invention, a measured amount of a chemical platelet activating factor or reagent 30 is provided in the top or upper reaction chamber 26 as a dried fill. This platelet activating factor composition is dissolved in the blood sample when the blood sample is introduced into the upper reaction chamber 26 and the clotting reagent 29 added and mixed therein. Additionally, selected amounts of heparin or protamine may be utilized as a dried fill in the reaction chamber 26, depending on the chemical procedure to be utilized.

In order to provide a series of differing clotting times, the amount of platelet activating factor in each cell differs from the amount in each other cell. In the first two cells 11A and 11B (as shown in FIG. 1), no platelet activating factor is utilized. In each succeeding cell 11C, 11D, 11E and 11F, increasing amounts of platelet activating factor or reagent are utilized.

The preferred platelet activating factor is the compound 1-O-alkyl-2-acetyl-sn-glyceryl-3-phosphorylcholine, a biologically active phospholipid. Other factors or compounds which may be used are collagen, epinephrine, ristocetin and arachidonic acid. Fills of the preferred platelet activating factor, 1-O-alkyl-2-acetyl-sn-glyceryl-3-phosphorylcholine, are prepared by mixing the factor with a saline (NaCl) solution containing 0.25% bovine serum albumin, and diluting with deionized water to the desired factor concentrations. An amount of each solution of the desired factor concentration is placed in a cell and allowed to evaporate, leaving a solid or dry fill residue of the desired amount of platelet activating factor. Desired amounts of heparin and protamine may also be added and dried as a fill.

The clotting reagent, such as kaolin, is prepared as a 4% w/v suspension in hydroxyethylpiperazine ethanesulfonic acid buffer with 0.5m calcium chloride, and sodium azide as a bacteriostatic agent. The amount of 0.088 ml of this clotting reagent is loaded into the reagent chamber 25 of each cell 11 of the cartridge 10.

In use, aliquots of 0.35 ml per cell of a blood sample are dispensed into each cell. This results in platelet activating factor (PAF) blood concentrations illustratively shown in the following Table.

TABLE I

Cartridge PAF Concentrations

| Cell A | Cell B | Cell C | Cell D | Cell E | Cell F |
|---|---|---|---|---|---|
| Amount of PAF in Platelet Function-PAF Cartridge ||||||
| 0.0 ng | 0.0 ng | 23 ng | 116 ng | 230 ng | 2.76 µg |
| Final Concentration of PAF in Blood ||||||
| 0.0 nM | 0.0 nM | 1.25 nM | 6.25 nM | 12.5 nM | 150 nM |

After introducing the blood samples in each cell reaction chamber, the clotting reagent is inserted into each reaction chamber and the clotting time of the blood in each cell is determined. From the clotting time for each cell, the clot ratio is calculated. Clot ratio is the ratio of the clotting times for cells C, D, E and F compared to the average control clotting times, Cells 11A and 11B. Platelet function is expressed as a percentage of the maximum clot ratio response observed in a normal population. This value of a normal population response is known and can be used to compute the clot ratio percentage which is in turn indicative of the platelet functionality. Any appropriate desired calculation may be made from the relative clotting times in each cell. The platelet functionality can in turn be utilized to determine blood loss during surgery and the need for a blood transfusion. The platelet functionality further assists in managing heparin therapy during cardiac surgery.

EXAMPLE I

Preparation of Platelet Activating Factor Solutions and Cells

1. Weigh out 62.5 mg Bovine Serum Albumin (BSA) (Sigma Product #A-3803).
2. Weigh out 219 mg NaCl.
3. Make up to 25 ml with deionized water. This gives 0.25% BSA/0.15 M NaCl. Leave until BSA is completely in solution.
4. Using a Hamilton syringe, pipette 50 µl platelet activating factor 1-O-alkyl-2-acetyl-snglyceryl-3-phosphorylcholine into a clean stoppered vial and allow to evaporate in a fume hood. Add 2 ml BSA/NaCl solution and leave at least 1 hour. This working stock material is at 100 µM.
5. Dilute the working stock platelet activating factor (PAF) in tenths serially down to 0.1 µM with deionized water. 5 µl of each of these solutions gives 1.25 µM, 12.5 µM, 125 µM and 1250 µM in 0.4 ml blood, respectively.
6. The following amounts are added to the cells and result in the indicated blood concentration:

| Cell | Reagent Added | Concentration of PAF |
|---|---|---|
| A | 5 µl BSA/NaCl | 0 nM |
| B | 5 µl 0.1 µM PAF | 1.25 nM |
| C | 5 µl 1 µM PAF | 12.5 nM |
| D | 5 µl 10 µM PAF | 125 nM |
| E | 2 µl 100 µM PAF | 500 nM |
| F | 5 µl 100 µM PAF | 1250 nM |

Figure 3:
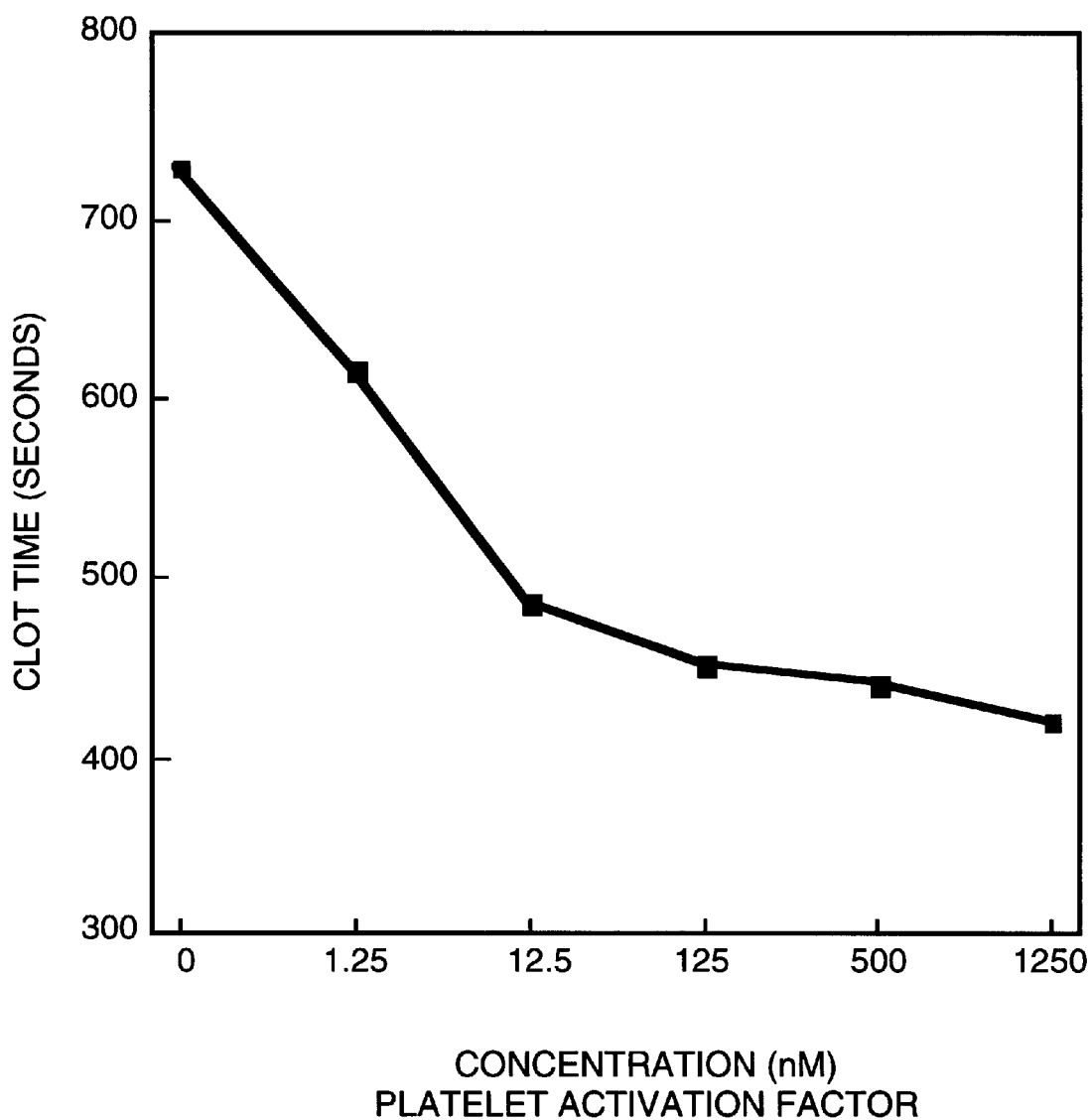
FIG. 3 is a diagram showing the relationship of platelet activating factor concentration to clotting time.

7. The water is allowed to evaporate, leaving a dry fill in each cell.
8. Using a sample of normal blood from a voluntary donor, and a cartridge prepared according to EXAMPLE I, 0.4 ml aliquots of blood were added to each cell and the clotting time of the blood in each cell was determined and plotted as FIG. 3.

As referred to above, the titration curve can be normalized by converting the clotting times to ratios. The clotting time of Cell A, with no platelet activating factor present, is the cell clotting time to which all other cell clotting times are compared. The ratio is calculated by dividing the Cell A clotting time in seconds by each other cell clotting time in seconds. A clot ratio is then calculated as 1 minus the ratio of Cell A clotting time to other cell clotting times (1—cellAtime/cellxtime). Data can also be presented in terms of platelet function as a percentage of normal. This is calculated from the clot ratio by multiplying the clot ratio by 100 and then by a factor of 1.97 which has been determined by measuring the maximum platelet activating factor response in 22 normal donors. These donors had no known platelet disfunction and were taking no known medications.

The test cartridge and method described herein are useful for providing a simple and rapid response point-of-care platelet function assay. This assay identifies patients with excessive post-cardiopulmonary bypass blood loss who could benefit from further blood treatment and management.

While a certain illustrative embodiment of the present invention has been shown in the drawings and described above in detail, it should be understood that there is no intention to limit the invention to the specific form disclosed. On the contrary, the intention is to cover all modifications, alternative constructions and compositions, equivalents and uses falling within the spirit and scope of the invention as expressed in the appended claims.

We claim:

1. An apparatus for indicating platelet functionality of a blood sample, said apparatus comprising a cartridge having a plurality of test cells, each said cell adapted for receiving an aliquot part of said sample, wherein each of said cells contains a sufficient amount of a clotting reagent to promote clotting, and a predetermined amount of a platelet activating reagent, the amount of said platelet activating reagent in each said cell differing from the amount of said platelet activating reagent in each other cell, wherein the relative clotting times of said aliquot parts of said sample in said cells are measured by a change in viscosity of said aliquot parts and are indicative of the platelet functionality of said sample.

2. An apparatus as defined in claim 1, wherein said platelet activating reagent is 1-O-alkyl-2-acetyl-sn-glyceryl-3-phosphorylcholine.

3. An apparatus as defined in claim 1, wherein said platelet activating reagent is selected from the group consisting of 1-O-alkyl-2-acetyl-snglyceryl-3-phosphorylcholine, collagen, epinephrine, ristocetin, and arachidonic acid.

4. An apparatus as in claim 1, wherein said change in viscosity is measured by a plunger sensor technique.

5. An apparatus for indicating clotting characteristics of a blood sample, comprising a cartridge having a plurality of test cells, each said cell adapted for receiving a aliquot of said sample, wherein each of said cells contains a sufficient amount of a clotting reagent to promote clotting, and a predetermined amount of a clotting affecting reagent, the amount of said clotting affecting reagent in each said cell differing from the amount of said clotting affecting reagent in each other cell, wherein the relative clotting times of said aliquots of said sample in said cells are measured by a change in viscosity of said aliquots and are indicative of the clotting characteristics of said aliquots.

6. An apparatus as defined in claim 5 wherein said clotting affecting reagent is a platelet activator.

7. An apparatus as in claim 5, wherein said change in viscosity is measured by a plunger sensor technique.

8. An apparatus for performing a platelet functionality test on a sample of blood, said apparatus comprising a plurality of test cells, wherein each of said cells comprises a sufficient amount of a clotting reagent to promote clotting and a predetermined amount of a platelet activating reagent, wherein at least two of tic test cells comprise different amounts of said platelet activating reagent, and wherein said platelet functionality is determined by measuring a change in viscosity of said sample.

9. An apparatus as defined in claim 8, wherein said platelet activating reagent is selected from the group consisting of 1-O-alkyl-2-acetyl-sn-glyceryl-3-phosphorylcholine, collagen, epinephrine, ristocetin, and arachidonic acid.

10. An apparatus as defined in claim 8, wherein said platelet activating reagent is 1-O-alkyl-2-acetyl-sn-glyceryl-3-phosphorylcholine.

11. An apparatus as defined in claim 8, wherein the amount of said platelet activating reagent in said cells is between about 0 and about 2.76 micrograms.

12. An apparatus as defined in claim 8, wherein the concentration of the platelet activating reagent in said cells is between about 0 and about 150 nM.

13. An apparatus as defined in claim 8, wherein at least one of said cells contains no platelet activating reagent, and wherein each remaining cell comprises different amounts of said platelet activating reagent.

14. An apparatus as defined in claim 8, wherein said clotting reagent is kaolin.

15. An apparatus as defined in claim 8, wherein the platelet functionality test is performed using a plunger sensor technique.

16. An apparatus for indicating clotting characteristics of a sample of blood, said apparatus comprising a plurality of test cells, wherein each of said cells comprises a sufficient amount of a clotting reagent to promote clotting and a predetermined amount of a clotting affecting reagent, wherein at least two of the test cells comprise different amounts of said clotting affecting reagent, wherein a relative clotting time of said sample is measured by a change in viscosity of said sample and is indicative of said clotting characteristics of said sample.

17. An apparatus as defined in claim 16, wherein said clotting reagent is kaolin.

18. An apparatus as in claim 16, wherein said change in viscosity is measured by a plunger sensor technique.

19. An apparatus as defined in claim 16, wherein said clotting affecting reagent is a platelet activating reagent.

20. An apparatus as defined in claim 19, wherein said platelet activating reagent is selected from the group consisting of 1-O-alkyl-2-acetyl-sn-glyceryl-3-phosphorylcholine, collagen, epinephrine, ristocetin, and arachidonic acid.

21. An apparatus as defined in claim 19, wherein said platelet activating reagent is 1-O-alkyl-2-acetyl-sn-glyceryl-3-phosphorylcholine.

22. An apparatus for performing a platelet functionality test on a sample of blood, said apparatus comprising a plurality of test cells, said cells being adapted for receiving an aliquot portion of said sample, wherein each of said cells comprises a sufficient amount of a clotting reagent to promote clotting and a predetermined amount of a platelet activating reagent, wherein at least two of the test cells comprise different amounts of said platelet activating reagent, and wherein a clotting time is determined for each of said aliquot portions, wherein the clotting time is based on a change in viscosity of said aliquots portions, and wherein the relative clotting times of said aliquot portions in said cells are determinative of the platelet functionality of said sample.

23. An apparatus as defined in claim 22, wherein said platelet activating reagent is selected from the group consisting of 1-O-alkyl-2-acetyl-sn-glyceryl-3-phosphorylcholine, collagen, epinephrine, ristocetin, and arachidonic acid.

24. An apparatus as defined in claim 22, wherein said platelet activating reagent is 1-O-alkyl-2-acetyl-sn-glyceryl-3-phosphorylcholine.

25. An apparatus as defined in claim 22, wherein said change in viscosity is measured by a plunger sensor technique.

* * * * *